US007181981B2

(12) United States Patent
Cohen Tenoudji et al.

(10) Patent No.: US 7,181,981 B2
(45) Date of Patent: Feb. 27, 2007

(54) ULTRASONIC TOMOGRAPH, SYSTEM AND METHOD FOR ULTRASONIC TOMOGRAPHIC MEASUREMENT USING SAME

(75) Inventors: Frédéric Cohen Tenoudji, Neuilly sur Seine (FR); Vincent Dewailly, Saint Michel sur Orge (FR); Jean-Pierre Frangi, Villejuif (FR); Jean-François Mourey, Cachan (FR)

(73) Assignee: Universite Paris 7 — Denis Diderot, Paris (FR)

( * ) Notice: Subject to any disclaimer, the term of this patent is extended or adjusted under 35 U.S.C. 154(b) by 96 days.

(21) Appl. No.: 10/482,874

(22) PCT Filed: Jul. 5, 2002

(86) PCT No.: PCT/FR02/02356

§ 371 (c)(1),
(2), (4) Date: May 7, 2004

(87) PCT Pub. No.: WO03/004978

PCT Pub. Date: Jan. 16, 2003

(65) Prior Publication Data
US 2004/0177693 A1    Sep. 16, 2004

(30) Foreign Application Priority Data
Jul. 6, 2001  (FR) ................... 01 09045

(51) Int. Cl.
*G01N 9/32* (2006.01)
(52) U.S. Cl. .................................. 73/861.28
(58) Field of Classification Search ............ 73/861.18, 73/861.19, 861.21, 861.22, 861.23, 861.24, 73/861.25, 861.26, 861.27, 861.28, 861.29, 73/861.31
See application file for complete search history.

(56) References Cited

U.S. PATENT DOCUMENTS 4,890,488 A    1/1990  Pincent et al.

(Continued)

FOREIGN PATENT DOCUMENTS

DE    196 33 558    2/1998

(Continued)

OTHER PUBLICATIONS

Lynnworth L C: "Clamp-on transducers for measuring swirl, cross flow and axial flow" Ultrasonics Symposium, 1994. Proceedings., 1994 IEEE Cannes, France Nov. 1-4, 1994, New York, NY, USA, IEEE, US, Nov. 1, 1994, pp. 1317-1321, XP010139793.

(Continued)

*Primary Examiner*—Hezron Williams
*Assistant Examiner*—Rose M. Miller
(74) *Attorney, Agent, or Firm*—Young & Thompson (57) ABSTRACT

The invention relates to an ultrasonic tomograph for spatial and temporal characterisation of fluids in motion such as air and water. This tomograph comprises a plurality of pairs of emitting-receiving ultrasonic probes, whereas each pair may be inscribed, diametrically opposite, on a circle centred round a flow axis of the fluid. The probes are therefore laid out on either side of the flow and will neither modify nor disturb the flow. Each probe may be displaced in a plane perpendicular to the flow axis. Indeed each probe is allocated a stepping motor. Each probe is a piezoelectric ceramic transducer which does not drift with time and which does not require any re-calibration, which provides the tomograph according to the invention stability over time. Moreover this tomograph is robust since these ultrasonic probes may be used under extreme conditions. The frequency of ultrasounds ranges between 30 kHz and 300 kHz.

25 Claims, 3 Drawing Sheets

U.S. PATENT DOCUMENTS

| | | | |
|---|---|---|---|
| 5,531,116 A * | 7/1996 | Chang et al. .................. | 73/597 |
| 5,531,124 A | 7/1996 | Kim et al. | |
| 5,705,753 A | 1/1998 | Hastings et al. | |
| 5,987,997 A * | 11/1999 | Roskam et al. .......... | 73/861.29 |
| 2002/0011120 A1* | 1/2002 | Huang ..................... | 73/861.25 |
| 2002/0166383 A1* | 11/2002 | Han et al. ..................... | 73/610 |

FOREIGN PATENT DOCUMENTS

| | | |
|---|---|---|
| FR | 2 628 216 | 9/1989 |
| GB | 1 591 216 | 6/1981 |

OTHER PUBLICATIONS

Bass H E et al: "Atmospheric absorption of sound: update" Journal of the Acoustical Society of America, Oct. 1990, USA, vol. 88, No. 4, pp. 2019-2021, XP001053675.

* cited by examiner

ULTRASONIC TOMOGRAPH, SYSTEM AND METHOD FOR ULTRASONIC TOMOGRAPHIC MEASUREMENT USING SAME

This invention relates to an ultrasonic tomograph for spatial and temporal characterisation of fluids in motion. It also relates to a system and a method for ultrasonic tomographic measuring by means of such a tomograph. It finds a particularly interesting application, but without being limited thereto, in industries and laboratories using measuring instruments for visualising a fluid flow and to assess the intrinsic characteristics thereof. This invention may be applied in any sector of activity requiring fine and quick investigations behind an object located most often in a wind tunnel.

Generally, tomography relates to the medical field, often radiology, wherein one wishes to obtain a sectional picture of a given organ. In this invention, one wishes notably to obtain the sectional picture of a fluid.

Medical ultrasound imaging devices, mainly based upon echographic techniques, are known, or still water tomography systems by reflected acoustic wave analysis. But as regards a use in the air for instance, these systems would require very powerful probes to be able to recover significant reflected signals, hence large-sized probes, which is a major shortcoming.

In the previous state of the art, there exist hot wire systems that are immersed in the fluid and which measure the variations in temperature of the probe during thermal exchange with the medium. There are also laser anemometers using the interferences between laser beams of the Doppler effect to determine the velocity of the particles in a fluid.

The document FR2 628 216 relates to an anemometer to determine a field of velocity by means of a device comprising several emitting and receiving probes. These probes are low frequency probes operating with wide frequency band ultrasonic signals.

However all the systems known remain intrusive or require the presence in the fluid of foreign particles. The laser system requires the introduction of thin particle into the fluid; it is moreover little practical. The Doppler ultrasound system is not intrusive, but it is used for studying microparticles in a fluid in a duct (blood in a vessel for instance). These methods may bring about certain perturbations in the object fluid to be measured, which may lead to biased results.

The purpose of this invention is to remedy the shortcomings aforementioned by offering a tomographic system wherein, not only the field of velocity may be determined, but also other characteristics such as humidity and temperature.

Another object of the invention is a non-intrusive device enabling to obtain optimised tomographic processing.

Another object of this invention is to provide a system which can be used under adverse weather conditions.

The objects mentioned above are met with an ultrasonic tomograph for characterisation of a fluid in motion. This tomograph comprises a plurality of pairs of emitting-receiving ultrasonic probes, whereas each pair may be inscribed, diametrally opposite, on a circle centred round a flow axis of the fluid. This way, the device according to the invention is not intrusive, the ultrasonic probes are situated on either side of the flow of the fluid and will neither modify nor disturb said flow unlike conventional velocity measuring systems (hot wired).

According to the invention, each probe comprises means for displacement on a plane perpendicular to said flow axis. Preferably, each circle is materialised by a ring carrying the probes. Consequently, the probes may be displaced on these rings by means of particularly accurate stepping motors. Advantageously, the rings are such that their diameters may vary. With such a device and for a given ring, one may proceed to measurements on ultrasound attenuation in diverse directions of a plane, ultrasound diffraction and the time taken by each ultrasonic signal to travel the distance between an emitting probe and a receiving probe. The device may be used in different gaseous or liquid media such as the air and water for instance.

The man of the art will understand easily that, the probes being liable to be displaced independently of one another, they do not remain strictly diametrally opposite, they may be displaced in order to analyse several points other than the central point of the circle. Ideally, the pair of probes is situated so that the receiving probe is capable of capturing the signal emitted by the emitting probe.

One may thus measure the characteristics of elementary volumes situated in the volume generated by the intersection of the different beams defined for each position of the set of two probes displaced on each circle. No probe is provided in the centre of each circle.

This invention involves advantageously a new parameter which is the bandwidth of the ultrasounds which is met either by the use of short pulses or by the use of wave trains of variable frequency. Indeed, to perform complete analysis with a fine resolution, wide band ultrasounds are sent, whereof the frequency ranges preferably substantially between 30 kHz and 300 kHz. It is however possible to operate the probes at lower frequencies, 1 kHz–100 kHz, which would prevent the application of the invention to larger volumes: of several tens of cubic metres. One may also measure the field of velocity, the size and the rotational of the vortices (eddies), the temperature and the humidity rate by acquisition of the different acoustic parameters: travelling time, attenuation, diffraction and refraction.

According to an embodiment of the invention, the device comprises at least one pair of emitting-receiving probes, whereas said first pair may be inscribed on a first circle perpendicular to said flow axis. A more complete variation may include a second pair which may be inscribed on a second circle forming an angle with the first circle. This disposition may be materialised by a ring of variable diameter carrying the first pair of probes on the same plane as this ring, and the second pair of probes outside the plane by means of two parallel arms and of opposite directions. Both emitting probes on the one hand and both receiving probes on the other hand may be interconnected and associated with a stepping motor capable of moving along the ring. Besides, this ring may carry at least three pairs of non-coplanar emitting-receiving probes and one may arrange two such rings parallel and centred round the flow axis.

To perform an analysis in the plane and in the volume, each ring may include means of spatial displacement, such as three stepping motors along three degrees of liberty. One may thus displace each ring in the plane in order to analyse each point of the plane, and one may also perform translations parallel to the flow axis of the fluid to perform a volume analysis.

According to a variation, the device may include a cylinder whereon is provided a plurality of rings carrying the pairs of probes.

According to a preferred embodiment of the invention, the probes comprise ionic transducers at emission and capacitive transducers at reception. They may also be piezoelectric ceramic transducers. The use of the probes aforementioned confers this invention stability over time since they do not require any re-calibration and do not drift with time. These probes also confer a robust character to this invention since they enable usage under extreme conditions: high or low temperature, pollution, high velocity.

The ionic and capacitive transducers exhibit the advantage of an excellent signal/noise ratio. The ionic transducers (dischargers) exhibit moreover a wide aperture and greater emission power than that of the piezoelectric probes over the range of the frequencies used. The capacitive transducers may prove besides less costly than the piezoelectric ceramics.

According to the invention, one may use for each pair of emitting-receiving probes, an emitting probe and a receiving probe; a probe which is emitting as well as receiving, connected to a mirror; or an emitting probe connected to a plurality of receiving probes. For the latter case, it is interesting to use as an emitting probe a wide aperture ionic transducer. Thus, at reception, one performs an electronic scan to recover the signal received by each receiving probe such as a capacitive transducer. One may also perform a mechanical scan: a single receiving probe moving in the radiation cone of the wide aperture ionic transducer.

According to another aspect of the invention, there is provided a system of ultrasonic tomographic measurement for characterisation of a fluid in motion by means of a tomograph as described above. According to the invention, this system comprises:

means for generating ultrasonic signals towards emitting probes of the tomograph,
means for power supplying and controlling the tomograph to manage the displacement of the set of probes of the tomograph,
processing means for capturing and processing the data from the tomograph.

The power supply and control means enable to supply the probes and the different motors of the tomographs, to communicate with the probes, and to actuate the stepping motors in order to displace the probes and the rings of the tomograph.

The means for generating ultrasonic signals may include a pulse generators and a pulse train generator, the latter being able to generate monochromatic signals or chirping-type variable frequency signals. Either generator may send a signal towards the tomograph over an ultrasonic signal amplifier.

Advantageously, the processing means may include a microcomputer which, on top of the task of managing the different movements of the sensors, and controlling the signal generators and the amplifiers, is fitted with means for capturing data from the tomograph and means for digitalising such data. The control and acquisition means may for instance be an input/output card (or several cards) connected to the probes of the tomograph, to the power supply and control means and to the generators. This card enables to send instructions towards the generators and the power supply and control means; this card or a second card enables to capture the signals from the probes. It is advantageous to provide high data generation rate as well as high frequency sampling in order to perform a fine analysis.

According to the invention, the microcomputer is fitted with signal processing means such as for instance the intercorrelation or the Fourier transform. It also comprises tomographic processing means to determine the characteristics of the flow of the fluid and to generate a picture which can be displayed on visualisation means such as a microcomputer screen.

An object of this invention is also an ultrasonic tomographic measuring method, implemented in a system as described above, for characterisation of a fluid in motion. According to the invention, around said fluid is placed a ring carrying, diametrally opposite, at least one pair of emitting-receiving probes, this ring forming a tomograph according to this invention, then:

a) an ultrasonic signal is sent towards the emitting probe and the signal captured by the receiving probe for a pre-set duration is recovered;

a') one may advantageously repeat step a) for a plurality of different positions of the receiving probe, which enables measurements for different acoustic axes;

b) the set of probes is pivoted several times by a given angle, and for each pivoting motion step a) is carried out;

c) the centre of rotation of the probes is moved elementarily in a plane XY and the steps a) and b) are carried out;

d) the set of signals captured by the receiving probe is subjected to tomographic processing in order to characterise the fluid in the main plane of the probes.

The set of probes may be pivoted by pivoting the ring whereas the probes are held fixedly, or by interconnected pivoting of the probes while holding the ring fixedly.

According to an embodiment of the invention, one may use a wide aperture emitting probe and several receiving probes arranged in the radiation cone of the emitting probe. One may then perform an electronic scan to recover the signal captured by each receiving probe.

Other advantages and characteristics of the invention will appear in the light of the detailed description of an embodiment, without being limited thereto, and of the appended drawings, whereon.

Figure 1:
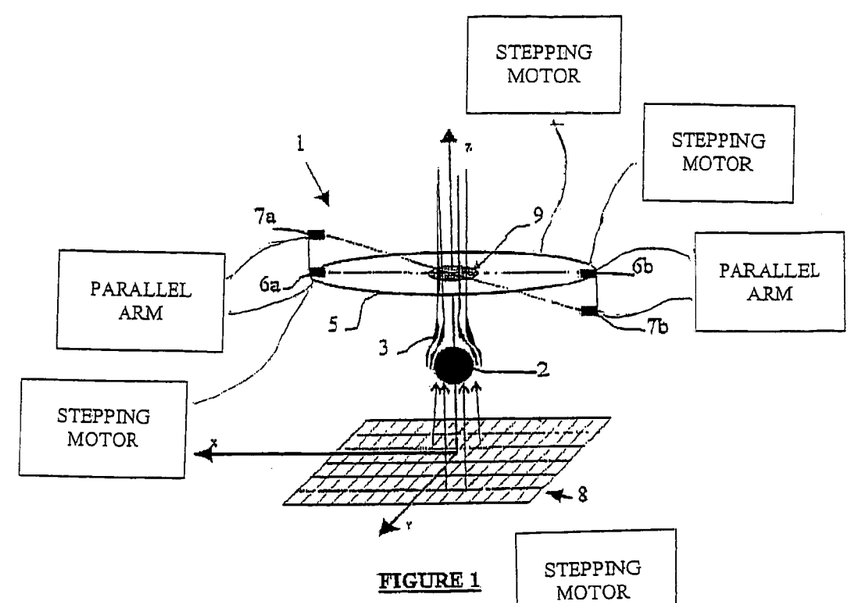
FIG. 1 is a simplified schematic view of a tomograph with two pairs of non-coplanar probes according to the invention.

With reference to FIG. 1, there is depicted a tomograph 1 according to the invention to characterise the flow of a fluid 3 created by an object 2 situated in a wind tunnel. The axis XYZ enables to define a fictitious grid 8 of tomographic displacement on the axis XY. The axis Z is a flow axis of the fluid 3.

The tomograph 1 consists notably of a ring 5 whereon are arranged two pairs of probes 6a, 6b, 7a and 7b. The pair of probes 6a, 6b comprises an emitting probe 6a and a receiving probe 6b arranged on a diameter of the ring. The pair of probes 7a, 7b consists of an emitting probe 7a and of a receiving probe 7b connected respectively to both probes 6a and 6b by means of two parallel and opposite arms. In other words, both pairs of probes are not coplanar and the straight lines running through both probes of each pair intersect at the centre of the ring through which runs the axis Z. The ring is in a plane perpendicular to this axis Z, and the arm connecting both emitting probes is parallel to this axis Z. Moreover, the probes 6a and 6b are attached to the ring 5, each probe by means of a stepping motor capable of moving on the ring 5. The fictitious zone 9 represents the surface studied. These are the spots of this surface which will be characterised.

Figure 2:
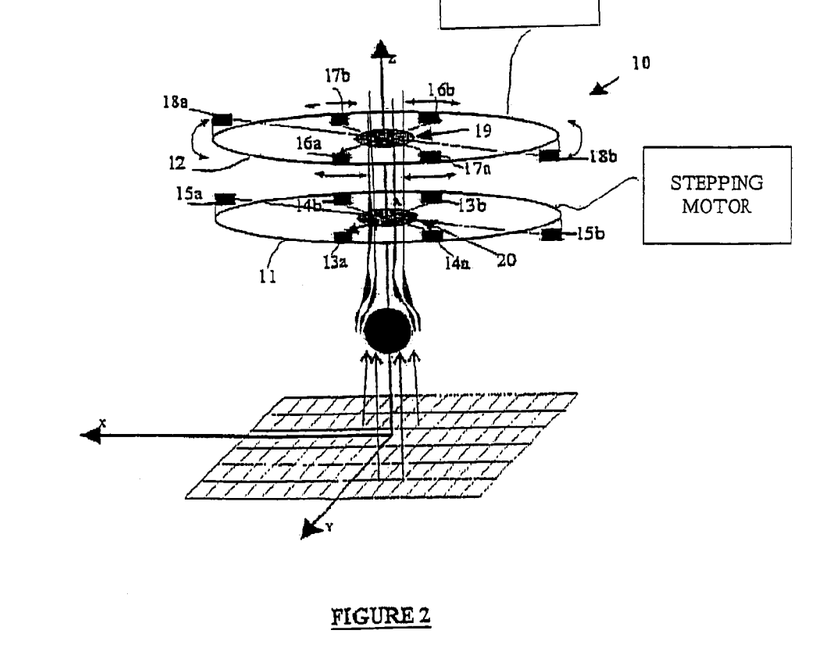
FIG. 2 is a simplified schematic view of a two-ring tomograph according to the invention.

On FIG. 2 is represented a tomograph 10 consisting of two rings 11 and 12 parallel and perpendicular to the flow axis Z, and centred round this axis. On this FIG. 2, only the tomograph differs from that of FIG. 1. Each ring 11, 12 comprises two pairs of coplanar probes 13a, 13b, 14a, 14b; 16a, 16b, 17a, 17b and a pair of probes 15a, 15b;18a, 18b mounted on two arms parallel to the axis Z and of opposite directions. Both pairs of probes 15a, 15b and 18a, 18b are not on the plane comprising their respective ring. The displacement of the probes is such that each probe is connected to a stepping motor capable of moving said probe on the corresponding ring independently of the other probes. Advantageously, both rings 11 and 12 are such that their diameter is variable thereby enabling to vary the distance between two probes of the same pair. Such a tomograph exhibits naturally two analysis surfaces 19 and 20.

One causes the distance between both planes to vary in order to observe the spatial variation of the properties of the fluid and of their spatial correlations.

The set of probes used in this invention may be piezoelectric ceramic transducers or ionic transducers at emission, and capacitive transducers at reception.

The tomographs thus described enable to analyse the central zone of each ring. For a complete analysis of the analysis surface 9, 19 and 20, three stepping motors are provided, capable of moving the rings 5, 11 and 12 along a plane parallel to the plane XY as well as along the axis Z. One skilled in the art will understand easily that it is possible to have more than two rings round the flow of the fluid in order to perform numerous measurements simultaneously.

Figure 3:
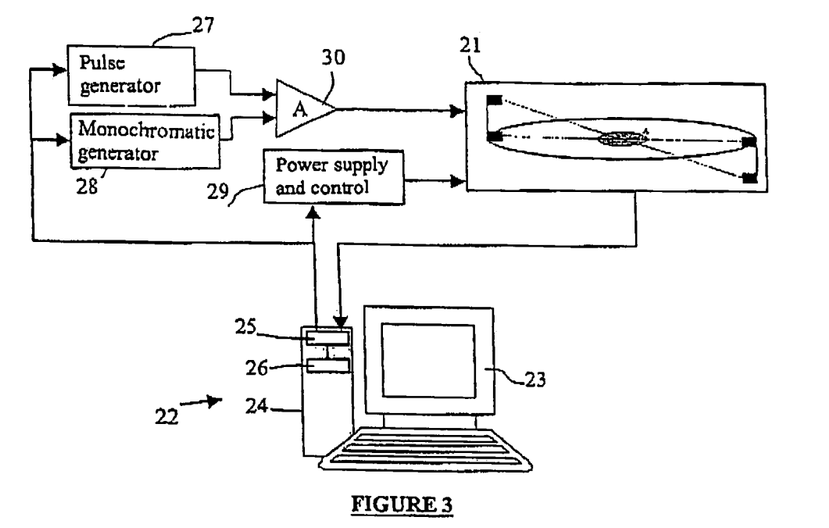
FIG. 3 is a general view of the system according to the invention comprising the tomograph and the means of analysis.
Figure 5:
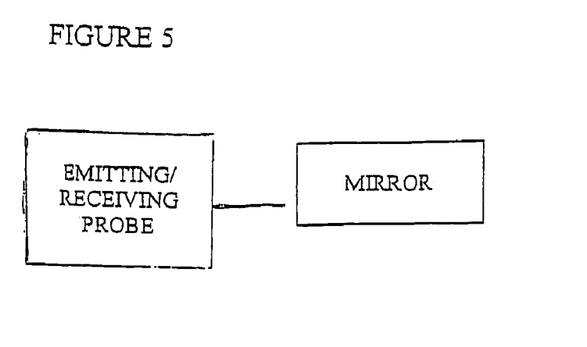
FIG. 5 schematically illustrates an emitting/receiving probe connected to a mirror.
Figure 6:
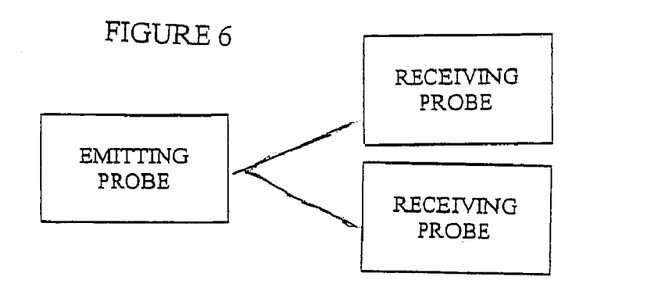
FIG. 6 schematically illustrates an emitting probe connected to a plurality of receiving probes.
Figure 7:
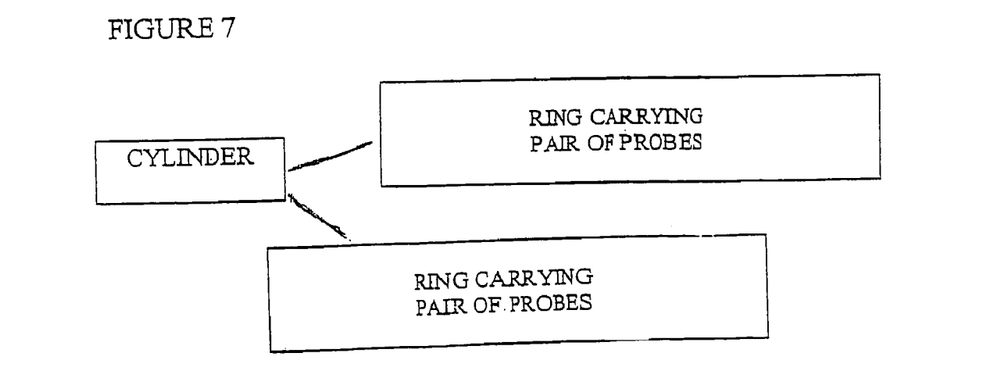
FIG. 7 schematically illustrates a cylinder whereon is provided a plurality or rings carrying pairs of probes.

With reference to FIGS. 1, 3 à 5, we shall now describe a mode of analysis to the invention. FIG. 3 is an overview of a system according to the invention. One distinguishes a tomograph 21 as described on FIG. 1. This tomograph 21 is driven by a microcomputer 22 fitted notably with a visualisation screen 23 and a central processing unit 24. This central processing unit 24 is fitted with means necessary to optimum operation such as for instance a high power microprocessor and memory capacities adapted to image processing systems. The central processing unit 24 comprises also an input/output card 25 to control the different displacements of the tomograph 21. The signals provided by the receiving probes are intended to be digitalised by a digitalising card 26 and then be subjected to several signal processing operations and tomographic processing operations. The input/output card 25 is also capable of transmitting instructions towards two ultrasonic signal generators 27 and 28, and towards a power supply and control unit 29 for the probes of the tomograph 21.

The generator 27 is a pulse generator capable of transmitting, in response to a setpoint from the microcomputer 22, a pulse signal such as a short-duration strobe.

It is therefore a multiple frequency signal.

The generator 28 is a generator capable of transmitting, in response to a setpoint of a microcomputer 22, a wave train, i.e. a train of frequency sine waves ranging from a few Hz to several hundreds of KHz for two seconds for instance.

Preferably the signals transmitted by both generators reach the emitting probes via an amplifier 30. Only a generator at a time may emit a signal notably because the microcomputer controls a single generator at a time.

Figure 4A:
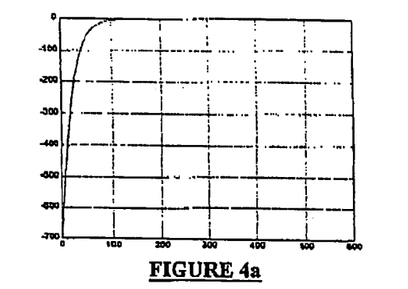
FIGS. 4a to 4d are graphs representing the processing of a signal acquired for the emission of a strobe or multi-frequency signal according to the invention.

We shall now describe a pulse mode analysis. The microcomputer instructs the generator 27 to generate multifrequency ultrasounds, i.e. a capacitor discharge having a discharge characteristic time of a few tens of microseconds. FIG. 4a is a graph illustrating such a pulse signal. This signal is transmitted towards the emitting probes 6a and 7a (FIG. 1) then diffused towards the receiving probes 6b and 7b.

The ultrasounds are very sensitive to the medium wherein they propagate (temperature, hygrometry, components of the atmosphere, velocity of the gas . . . ). It is therefore from this sensitivity that information will be extracted on the thin structures of the turbulence and the hygrometry of the fluid 3. By measuring the arrival time, the attenuation, the diffraction and refraction of a wide band ultrasonic wave (30 kHz–300 KHz) transmitted between an emitting probe and a receiving probe, we shall obtain cartography of the attenuation, of the field of velocity and of the refraction. These acoustic parameters will enable us to derive local information on the size and velocity of rotation of the vortices (eddies), on the temperature and on the humidity.

Each signal captured by the receiving probe 6b or 7b is recovered by the micro-computer 22 via the digitalising card 26, then a signal processing. Digitalising may be performed with a 4 MHz sampling frequency for instance. Higher sampling frequencies may advantageously be used.

Figure 4B:
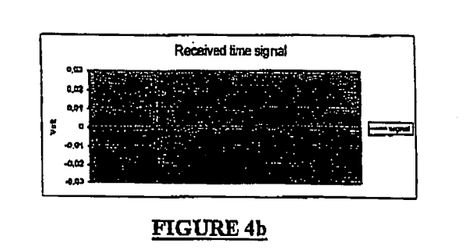
Figure 4C:
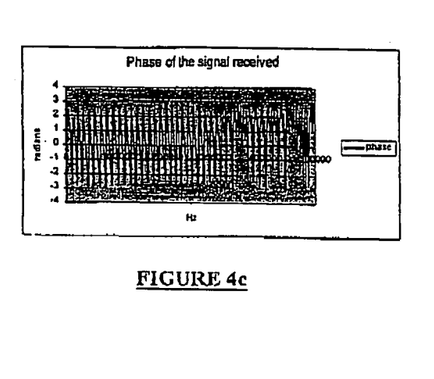
Figure 4D:
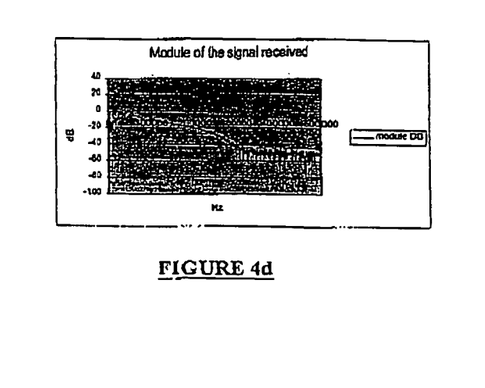

Processing a signal consists notably in calculating the time taken by the ultrasonic wave to travel the distance between two probes and the attenuation during said travel. One uses techniques known as such to perform these calculations. Processing the signal may also consist in performing a Fourier transform of each signal received. It can be seen on FIG. 4b a time signal received by one of the receiving probes, and FIGS. 4c and 4d correspond respectively to the phase and to the module of the spectrum of the Fourier transform of this signal.

A range of extended information on the movements of the fluid is provided by the study of the phase (FIG. 4c) over a frequency range between 30 kHz and 300 kHz (followed by the advance or the delay caused by the movements at the different frequencies).

The study of the module (FIG. 4d) provides information on the attenuation of the ultrasonic waves at the various spectral components, this attenuation being due to the diffusion of the ultrasounds on the vortex, to the refraction of the wave on the field of velocity and to the relaxation of the molecules contained in the fluid.

This study of the phase and module is carried out on each signal received and for each position of the probes. Indeed, one performs a measurement for different positions of the probes. For instance, for the pair of probes 6a and 6b arranged on the diameter of the ring 5, one sends a pulse signal of 6a towards 6b. One may record each signal received or record an average on a more or less large number of signals received for a given position of the probes. The first method enables to study the statistic of a signal and therefore to study the time variations of the signals, the second method enables to study the permanent rating of the flow of the fluid. Then, one moves the receiving probe 6b by using the associated stepping motor, by a few degrees on either side from its initial aligned position. In each position, one performs an average of the signal. To study, for instance, the influence of the turbulent flow on the diffraction, one performs approximately ten measurements around the aligned position.

Then, one brings the receiving probe 6b back to its initial position and one rotates the whole ring by an angle selected in relation to the accuracy desired of the measurement of the parameters. Then, one repeats the measurements as described above. The ring will be finally pivoted into four positions, i.e. some forty measurements. This forms a study of diffraction for the central spot of the ring 5. One then moves the whole tomograph along the plane grid 8 in order to overlap the centre of the ring 5 with different points of the analysis surface 9. For each point one performs measurements as aforementioned. These points may for instance correspond to the points of intersection of the lines of the grid 8.

The set of signals captured will be used for ultrasonic tomographic analysis according to the invention whereof the details are mentioned below:

I) Determination of the Fields of Velocity and of Attenuation:

1) During step a) defined previously, for a given position of a couple of probes whereof the direction of the acoustic axis is indicated by the angle θ, the attenuation $A_\theta(t,f)$ at a measuring instant t, and a frequency f is given by:

$$A_\theta(t, f) = \frac{1}{l_a} \int_{l_a} a(s, t, f) ds$$

where the curvilinear abscissa is noted s along the acoustic path of length $l_a$ and $a(s,t,f)$ is the attenuation of the element ds.

The phase shift $\Delta\phi_\theta(t,f)$ at the same instant t, and at the frequency f is moreover given by:

$$\Delta\varphi_\theta(t, f) = -2\pi f \int_{l_a} \frac{ds}{c(s, t, f)}$$

where $c(s,t,f)$ is the-local superaudible velocity, $A_\theta(t,f)$ and $c(s,t,f)$ are random time variables integrating the properties of the fluid on the line of propagation specified by θ. The mathematical expectancy of these variables enables to reach conventionally the average properties of the fluid: average velocities in the flow, and average attenuation. The correlation functions (self- correlation for the same receiving probe, intercorrelation between the signals provided by two receiving probes) enable to perform temporal spectral analysis of the turbulent signals.

2) The results of the angular analysis performed in step a') defined previously by the scanning of the receiving probe lead to a first assessment of the volume of refracting fluid. One may determine a length of spatial correlation and to perform spectral analysis of the spatial variations in the volume of fluid scanned.

3) The measurements are carried out while rotating the direction of ultrasonic propagation and while displacing the tomograph in its plane.

One switches from results on the functions of line $A_\theta(t,f)$ and $c(s,t,f)$ to the results for each of the elementary volumes forming this volume by the conventional tomography methods (Radon transform or iterative digital methods for minimisation of the assessment error).

One then reaches the value of the functions $a(r_i,t,f)$ and $v(r_i,t,f)$ where $r_i$ is the position vector of the elementary volume i and v designates the velocity vector at this point.

The results are presented in the form of pseudo-colour images.

II) Determination of the Field of Temperature and of Velocities:

In the case of stationary temperature, one reverts moreover the role of the transmitter and of the receiver and one measures thus the absolute celerity given by the formula $c=\sqrt{\gamma RT}$ where the atmosphere is considered as a mixture of perfect gases.

$$(\gamma = \frac{7}{5}$$

is the ratio of the specific heats of the gases at constant pressure and at constant volume, $R=8.31$ $JK^{-1}$ is the Robert Mayer constant and T the absolute temperature).

$$t_1 = \frac{d}{c+v},$$

$t_1$ corresponds to the time taken by the wave to travel the distance d between the transmitter and the receiver, v being the velocity of the fluid in the transmitter-receiver direction and c the celerity of the ultrasounds depending moreover on the temperature.

After reversing the role of the transmitter and of the receiver, one measures $$t_2 = \frac{d}{c-v}.$$

$t_2$ corresponds to the time taken by the wave to travel the distance d between the transmitter and the receiver, the velocity component on the axis of both probes is opposite −v. From both these equations one derives c. Knowing c, one obtains therefore easily the integral value of the velocity of the fluid v. If the velocity v is null, one reaches directly the value of the temperature if not, the tomographic analysis enables to go back to the value of c and therefore to the local value of T.

Using a tomography algorithm (rotation and or translation of the emitting and receiving probes), one obtains the field of temperature and of velocities of the study zone.

III) Determination of the Field of Humidity:

In a resting atmosphere, the attenuation of the sound α at the frequency f expressed in Neper per meter is written thus:

$$\alpha = f^2 \left[ 1.84 \cdot 10^{-11} \left(\frac{p_s}{p_{s0}}\right)^{-1} \left(\frac{T}{T_0}\right)^{1/2} + \left(\frac{T}{T_0}\right)^{-5/2} \{1.278 \cdot 10^{-2} \right.$$

$$[\exp(-2239.1/T)] / \left[f_{r,O} + \left(\frac{f^2}{f_{r,O}}\right)\right] + 1.068 \cdot 10^{-1} \cdot$$

$$[\exp(-3352/T)] / \left[f_{r,N} + \left(\frac{f^2}{f_{r,N}}\right)\right]$$

where $p_s$ is the pressure in the gas, $p_{s0}$ is the reference pressure (1 atm)

T is the temperature and $T_0$ is the reference temperature (293,15 K). $f_{r,O}$ is the molecular relaxation frequency of the oxygen molecule, $f_{r,N}$ that of nitrogen which are assessed relative to the molar concentration of water steam h expressed in percentage and given by the relations:

$$f_{r,O} = \left(\frac{p_s}{p_{s0}}\right)[24 + 4.04 \cdot 10^{-4} h(0.02 + h) \cdot (0.391 + h)^{-1}]$$

$$f_{r,N} = \left(\frac{p_s}{p_{s0}}\right)\left(\frac{T_0}{T}\right)^{1/2}\left\{9 + 280 h \exp\left\{-4.17\left[\left(\frac{T_0}{T}\right)^{1/3} - 1\right]\right\}\right\}$$

These expressions to determine the field of humidity are notably recorded in the article of H. E Bass, L. C. Sutherland and A. J. Zuckerwar, Atmospheric absorption of sound: Update, J. Acoust. Soc. Am, 88(4), pp. 2019–2021 (1990).

The measurement of the relative humidity h will be derived from the measurement of the variation in amplitude relative to the frequency obtained for different distances between the emitting-probe receiving-probe pair.

According to other variations of the invention, instead of the pulse signal, one may send some ten cycles of a sine wave at a given frequency, or send a train of a sine wave whereof the frequency varies with time (chirping signal)

Obviously, the invention is not limited to the examples which have just been described and numerous amendments may be made to these examples without departing from the framework of the invention.

The invention claimed is:

1. An ultrasonic tomograph for measuring characteristics of elementary volumes of a fluid in motion, comprising a plurality of pairs of emitting-receiving ultrasonic probes, whereas each pair may be inscribed on a circle round a flow axis of said fluid, characterised in that each probe comprises means for displacement independently of the other probes on a plane perpendicular to said flow axis.

2. A device according to claim 1, characterised in that it comprises at least one pair of emitting-receiving probes, whereas said first pair may be inscribed on a first circle perpendicular to said flow axis, and a second pair may be inscribed on a second circle forming an angle with the first circle.

3. A device according to claim 2, characterised in that it comprises a ring of variable diameter carrying said first pair of probes on the same plane as said ring, and the second pair of probes outside the plane by means of two parallel arms and of opposite directions.

4. A device according to claim 1, characterised in that it comprises at least two parallel rings and centred round said flow axis, each ring being of variable diameter and carrying at least three pairs of non-coplanar emitting-receiving probes.

5. A device according to claim 4, characterised in that each ring comprises means of spatial displacement.

6. A device according to claim 5, characterised in that the means of displacement comprise three stepping motors along three degrees of liberty.

7. A device according to claim 1, characterised in that the probes comprise piezoelectric ceramic transducers.

8. A device according to claim 1, characterised in that the probes comprise ionic transducers at emission, and capacitive transducers at reception.

9. A device according to claim 1, characterised in that each probe is allocated a stepping motor.

10. A device according to claim 1, characterised in that each pair of probes is composed of a probe which is emitting as well as receiving, connected to a mirror.

11. A device according to claim 1, characterised in that each pair of probes is composed of an emitting probe connected to a plurality of receiving probes.

12. A device according to claim 1, characterised in that it comprises a cylinder whereon is provided a plurality of rings carrying said pairs of probes.

13. System of ultrasonic tomographic measurement for characterisation of a fluid in motion by means of a tomograph according to claim 1, characterised in that it comprises:
   means for generating ultrasonic signals to emitting probes of the tomograph,
   means for power supplying and controlling the tomograph to manage the displacement of the set of probes of the tomograph,
   processing means for capturing and processing the data from the tomograph.

14. A system according to claim 13, characterised in that the means for generating ultrasonic signals comprise a pulse generator.

15. A system according to claim 13, characterised in that the means for generating ultrasonic signals comprise a pulse train generator.

16. A system according to claim 13, characterised in that it comprises moreover an amplifier of said ultrasonic signals.

17. A system according to claim 13, characterised in that the processing means comprise a micro-computer fitted with means for acquisition of data from tomograph and means for digitalising said data.

18. System according to claims 17, characterised in that the micro-computer comprises means to operate said means for generating ultrasonic signals as well as said power supply and control means.

19. A system according to claim 17, characterised in that the micro-computer comprises signal processing means and tomographic processing means.

20. System according to claim 19, characterised in that the micro-computer is connected to display means.

21. An ultrasonic tomographic measuring method, implemented in a system according to claim 13, for characterisation of a fluid in motion, characterised in that around said fluid is placed a ring carrying, diametrically opposite, at least one pair of emitting-receiving probes, said ring forming a tomograph comprising a plurality of pairs of emitting-receiving ultrasonic probes, whereas each pair may be inscribed, diametrally opposite, on a circle centred round a flow axis of said fluid, characterised in that each probe comprises means for displacement on a plane perpendicular to said flow axis; the method comprising the steps of:
   a) an ultrasonic signal is sent towards the emitting probe and the signal captured by the receiving probe for a predetermined duration is recovered;
   b) the set of probes are pivoted several times by a given angle, and for each pivoting motion step a) is carried out;
   c) the centre of rotation of the probes is moved elementarily in a plane XY and the steps a) and b) are carried out;
   d) the set of signals captured by the receiving probe is subjected to tomographic processing in order to characterise the fluid in the main plane of the probes.

22. A Method according to claim 21, characterised in that before step b), step a) is repeated for a plurality of different positions of the receiving probe.

23. A method according to claim 21, characterised in that a wide band ultrasonic signal is sent.

24. A method according to claim 23, characterised in that the frequency of the wide band ultrasonic signal ranges substantially between 30kHz and 300KHz.

25. A method according to claim 1, characterised in that one uses a wide aperture emitting probe and several receiving probes arranged in the radiation cone of the emitting probe, and in that one performs an electronic scan to recover the signal captured by each receiving probe.

* * * * *